(12) United States Patent
Wai (10) Patent No.: US 6,349,590 B1
(45) Date of Patent: Feb. 26, 2002

(54) METHOD AND APPARATUS FOR ESTIMATING LOAD BEARING CAPACITY OF PILES

(76) Inventor: Yee Kong Wai, 18-3 A, Jalan Pandan 3/7, Pandan Jaya, Kuala Lumpur (MY)

( * ) Notice: Subject to any disclaimer, the term of this patent is extended or adjusted under 35 U.S.C. 154(b) by 0 days.

This patent is subject to a terminal disclaimer.

(21) Appl. No.: 09/580,390

(22) Filed: May 26, 2000

Related U.S. Application Data (63) Continuation-in-part of application No. 09/153,549, filed on Sep. 15, 1998, now Pat. No. 6,082,173.

(30) Foreign Application Priority Data

Sep. 15, 1997 (MY) .......................................... PI9704268

(51) Int. Cl.[7] .............................................. G01N 33/00
(52) U.S. Cl. ......................................................... 73/84
(58) Field of Search ............................ 73/12.01, 12.06, 73/12.09, 12.13, 78, 81, 82, 84

(56) References Cited

U.S. PATENT DOCUMENTS

| | | | |
|---|---|---|---|
| 2,496,420 A | | 2/1950 | Stern |
| 2,531,388 A | | 11/1950 | Black |
| 3,817,091 A | * | 6/1974 | Frederick ........................ 73/84 |
| 3,879,982 A | | 4/1975 | Schmidt |
| 3,946,598 A | | 3/1976 | Towne et al. |
| 3,960,008 A | * | 6/1976 | Goble et al. .................... 73/84 |
| 4,054,339 A | * | 10/1977 | Ladin .......................... 384/569 |
| 4,313,337 A | | 2/1982 | Myint |
| 4,359,890 A | | 11/1982 | Coelus |
| 4,531,400 A | | 7/1985 | Nevel |
| 4,845,996 A | * | 7/1989 | Bermingham ................ 73/807 |
| 6,082,173 A | * | 7/2000 | Wai ........................... 73/12.13 |

OTHER PUBLICATIONS

Hussein et al. *Testing Methods of Driven Piles*. Pile Buck, Inc, 1988.

"Home Page," "Introduction," and "Articles and Technical Monographs" from Website entitled "The Wage Equation Page for Piling" at http://www.geocities.com/CapeCanaveral/Hanger/2955/, last revised Aug. 5, 2000.

Yu, Richard and Leong, Ching "Evaluation of Static Pile Capacity for Different Piles by Dynamic Testing", Bulletin IEM, Dec. 1989.

S. L. Lee et al., "Dynamic testing of Bored Piles for Suntec City Development", Conference on Deep Foundation Practice in Singapore, Oct. 1990.

British Standard Code of Practice for Foundations (BS 8004: 1986); British Standards Institution; pp. 84–109.

Bowles, Joseph E. "Foundation Analysis and Design"; 4th Edition, McGraw–Hill Book Company, 1988, Chapter 17, pp. 785–820.

\* cited by examiner

*Primary Examiner*—Max Noori
(74) *Attorney, Agent, or Firm*—Merchant & Gould P.C.

(57) ABSTRACT

A method for estimating the load bearing capacity of a pile using an Impact Load formula including obtaining the values of the weight of an impact mass, the stroke height of the impact mass, the length of the pile, the cross sectional area of the pile, and the Young's modulus of the pile. A preferred derived formula is $$P = \sqrt{\frac{2hAEW}{L_e}} \quad \text{Formula II}$$

wherein

R=soil-resistance load or end-load bearing;

W=the weight of hammer;

h=the height of hammer stroke;

$L_e$=the length of pile;

A=the cross sectional area of pile;

E=the Young's modulus of pile.

A computational tool for applying this method in the form of a portable or virtual calculator is disclosed. An apparatus set-up for on-line in situ testing of piles employing the method comprising a portable computer, data acquisition module and transducers is also disclosed.

15 Claims, 4 Drawing Sheets

FIG. 1
PRIOR ART

LEGEND
R = PILE BEARING CAPACITY
W = HAMMER WEIGHT
h = HAMMER STROKE
s = SET PER BLOW
$L_c$ = EFFECTIVE PILE LENGTH
A = PILE CROSS-SECTIONAL AREA

LEGEND
- R = LOAD BEARING CAPACITY
- W = HAMMER WEIGHT
- h = HAMMER STROKE
- x = SET/ELONGATION PER BLOW
- L = LENGTH OF PILE/STRUCTURE
- A = PILE/STRUCTURE CROSS-SECTIONAL AREA

FIG. 4
PRIOR ART

METHOD AND APPARATUS FOR ESTIMATING LOAD BEARING CAPACITY OF PILES

CROSS REFERENCE TO RELATED APPLICATION

This application is a continuation-in-part of U.S. Ser. No. 09/153,549 filed on Sep. 15, 1998 now U.S. Pat. No. 6,082,173 based on Malaysian patent application No. PI9704268 filed on Sep. 15, 1997.

TECHNICAL FIELD

This invention relates to a method for estimating the load-bearing capacity of a pile. It includes a method and apparatus for predicting the capacity or load bearing of a proposed or virtual pile, and a method and apparatus for measuring the estimated load bearing of an actual driven pile, including means for acquiring data from a pile being driven or an installed pile for the purposes of applying the present method to estimate its load bearing.

BACKGROUND ART

Of the few categories of foundation pile installation methods (such as driven, bored, injected, cast-in-place, caisson or floating, etc.) the method of this invention is based on the impact-driven or hammer-driven testing on an installed pile or pile under installation.

As the load bearing capacity of a pile is of the utmost importance in considering the design and installation of a building structure's foundation, various methods have been employed to estimate the pile's load bearing capacity. As the ultimate load bearing of a foundation is limited by either the structural strength of the pile or the capacity of the supporting soil (i.e. the "pile-soil" system), geotechnical engineers may, in most instances, choose or design the appropriate piles. The soil factor, on the other hand, are but predetermined by the proposed structure's site and, hence, the soil profile can only be analysed and studied through soil tests.

The manner in which the adequacy of a pile chosen or designed in meeting the allowable loads is generally governed by building by-laws or standards such as the BS 8004:1986. The pile's load bearing capacity may then be verified by one or more of the conventional tests such as static tests, dynamic tests or wave equation-based tests.

Static Test

Traditionally, the most relied upon pile testing has been the static load test which involves waiting for up to 30 days after pile driving to allow soil remoulding and settlement before stacking incrementally static weight loads onto the pile top and then measure the corresponding pile movements. In practice, static tests are performed to either (i) prove that it can safely hold the design load (proof test), or (ii) to determine a design load based on the ultimate load bearing capacity of the pile (i.e. load until failure).

Proof testing is more prevalent as the ultimate pile strength may often never be known. This results in higher capacity of the piles being laid and thus incurring greater foundation costs than are actually required. Moreover, due to the physical difficulty of stacking large weight blocks onto the pile top, the length of time and costs involved, only a small percentage of the piles on site are actually tested.

Dynamic Test

From the number of hammer blows in advancing a pile per unit of penetration, the energy from the hammer blows has been equated to the work done in advancing the pile against soil resistance. Based on Newton's Second Law of Motion, i.e. the impulse-momentum principles, theoretical and semi-empirical formulae have been derived to express this relationship between energy and work by assuming the hammer and pile are rigid bodies and soil resistance as a constant static force. These formulas are generally known as Dynamic Formulae or Energy Formulae.

Figure 1:
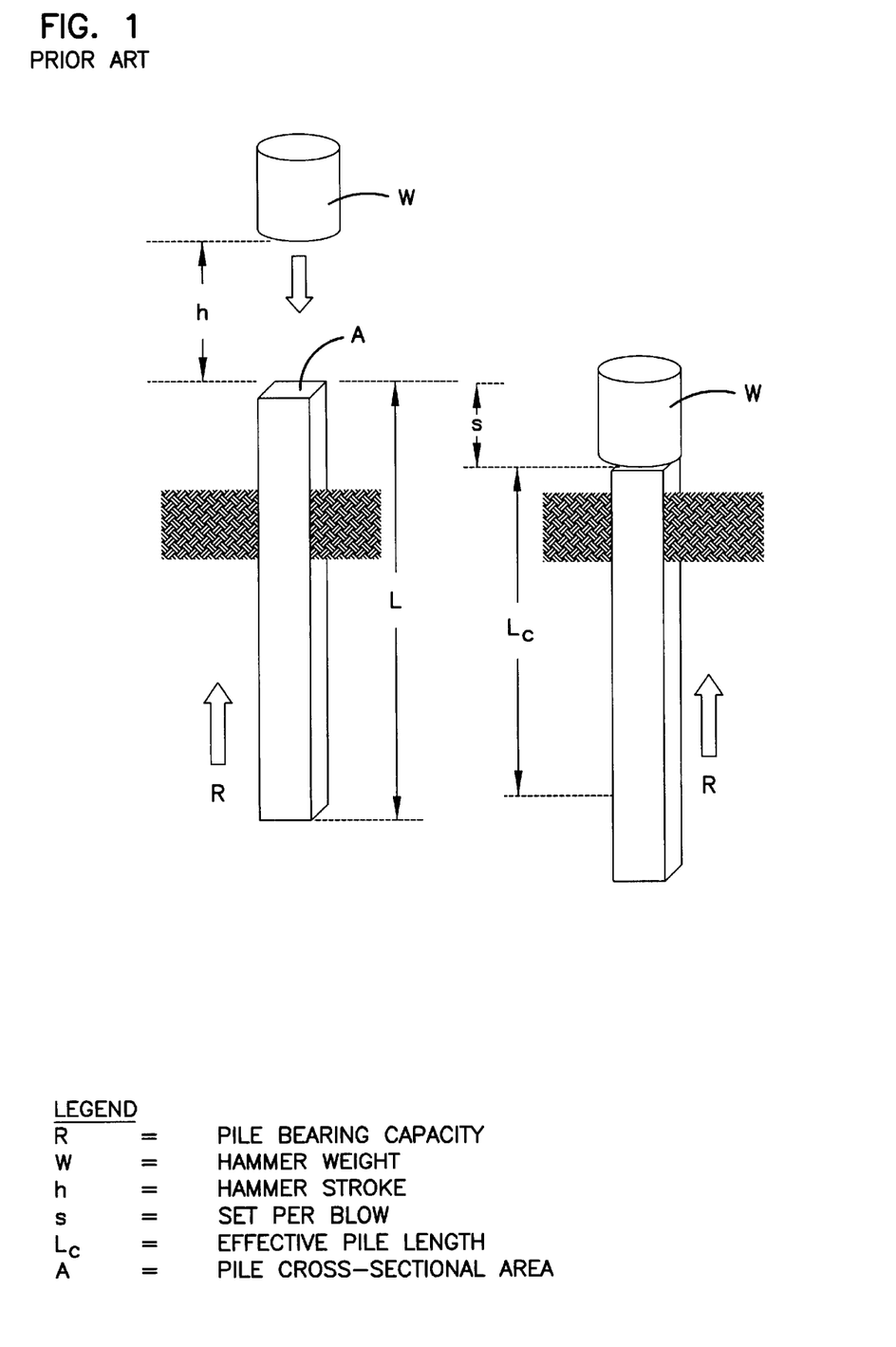
FIG. 1 (prior art) shows a physical representation of a simplified Dynamic Formula described hereinbefore in the Background Art.

The model common to all the simple dynamic formulae may be illustrated in FIG. 1 where if potential energy stored in the ram is equated to the work done by advancing the pile against a constant soil resistance, then $$Wh = Rs.$$

or $$R = \frac{Wh}{s}$$

where $W$ is the ram weight;

$R$ is the soil resistance constant;

$h$ is the drop height of the ram;

$s$ is the pile set.

This basic dynamic pile capacity formula, which is also termed "rational pile formula", and most of the other dynamic pile formulae currently in use are derived from this equation. [For examples, see Joseph E. Bowles, *Foundation Analysis and Design*, 4th edition, McGraw-Hill, 1988, p. 791].

The more common formulas derived from the above rational pile formula have incorporated various assumptions on certain parameters in order to improve on the reliability of predictions on the pile capacity; however, each formula gives a different value of the capacity of the same pile. Some are these formulas are given in the following Table 1 [from Bowles, p. 794].

TABLE 1

VARIOUS DYNAMIC PILE FORMULAS

Danish formula [Olson and Flaate (1967)](use SF = 3 to 6)

$$P_u = \frac{e_h E_h}{s + C_1}; \text{ wherein } C_1 = \sqrt{\frac{e_h E_h L}{2AE}}$$

Eytelwein formula (use SF = 6) [Chellis (1961)]

$$P_u = \frac{e_h E_h}{s + 0.1\left(\frac{W_p}{W_r}\right)}$$

Modified ENR [Engineering News-Record (1965)] (use SF = 6)

$$P_u = \frac{1.25(e_h E_h)}{s + 0.1} \cdot \frac{W_r + n^2 W_p}{W_r + W_p}$$

Hiley Formula (1930)

$$P_u = \frac{e_h W_r h}{s + \frac{1}{2}(k_1 + k_2 + k_3)} \cdot \frac{W_r + n^2 W_p}{W_r + W_p}$$

wherein
$P_u$ = ultimate pile capacity, F.
$A$ = pile cross-section area, $L^2$.
$E$ = modulus of elasticity, $FL^{-2}$.
$e_h$ = hammer efficiency.
$E_h$ = manufacturers' hammer-energy rating, FL.

TABLE 1-continued

VARIOUS DYNAMIC PILE FORMULAS h = height of fall of ram, L.
$k_1$ = elastic compression of cap block and pile cap and is a form of $P_uL/AE$, L.
$k_2$ = elastic compression of pile and is of a form of $P_uL/AE$, L.
$k_3$ = elastic compression of soil, also termed quake for wave-equation analysis, L.
L = pile length, L.
n = coefficient of restitution.
s = amount of point penetration per blow, L.
$W_p$ = weight of pile including weight of pile cap, driving shoe, and cap block (also includes anvil for double-acting steam hammers), F.
$W_r$ = weight of ram (for double-acting hammers include weight of casing), F.

Each of the formulas has its own advantages under different circumstances. For example, the Engineering News-Record (ENR) formula (1965) is thought to be reasonably valid over the entire range of load tests and has been cited as the most widespread dynamic formula in the U.S.A. It defines the soil resistance, R, in terms of the ultimate pile capacity, $P_u$, as the safe load in kips (1 kip=1000 lbs=453.6 kg) with "loss" terms $e_h$ and $E_h$ introduced and safety factor (SF) of 6 assigned. [Hussein, Likens & Rausche, *Testing Methods of Driven Piles*, Pile Buck, Inc., 1988].

The Hiley formula (1930) is found to have the least statistical deviation or the highest statistical correlation. In fact, the British Standard BS 8004:1986 cites the Hiley formula as one of the more reliable dynamic formulas and is probably the most commonly used in Britain.

Although dynamic formulas have been widely used to predict pile capacity, more accurate means is needed to determine when a pile has reached a satisfactory load-bearing value other than by simply driving it to some depth predetermined by the formulas. The pile driven to a predetermined depth may or may not obtain the required bearing value due to the complex pile and soil characteristics. Today, dynamic formulas are generally acknowledged as inaccurate due to their oversimplification of the modelling of the hammer, driving system, pile, and soil. In fact, they are not applicable to most hammer types used on today's sites, long elastic piles, or cohesive, impermeable, compressible soils.

Wave Equation Analysis

Modern foundation engineering recognises that pile driving may be better estimated by wave propagation theories which may include complicated partial differential equations With the advent of digital computers in the 1950s it became possible to arrive at a discrete solution of wave propagation equations by algorithm using computer program codes, thus allowing for pile driving analysis.

Examples of such wave equation analysis programs widely used today are WEAP, WEAP86 and TTI which were developed under the U.S. Federal Highway Administration's sponsorship in the 1960s. Further development and refinement lead to commercially available programs such as the following examples.

GRLWEAP™ from Goble Rausche Likins and Associates, Inc. (GRL) and used often in analyses prior to actual pile installation. It has been claimed as the most widely used wave equation in predicting pile bearing capacity and driveability. It has also been used for analyses and selection of proper pile installation equipment prior to the installation of piles, CAPWAP™ (including its modifications such as CAPWAPC™, etc.) or Case Pile Wave Analysis Program which was developed from the research conducted by Prof. G. G. Goble, F. Rausche and G. Likins which begun in 1964 at Case Institute of Technology, now Case Western Reserve University; hence also known as the Case Method. It is often used in analyses during and after pile installation in conjunction with a wide array of instrumentation system for field measurement from Pile Dynamics, Inc. (PDI); both the companies, GRL and PDI, based at Cleveland, Ohio, U.S.A., grew from Prof Goble's the core research team;

TNOWAVE™ from TNO Building & Construction Research, Delft, Netherlands;

SIMBAT™ from Testconsult Ltd., Warrington, United Kingdom; etc.

Each of the above examplary methods uses slightly different modelling of the pile-soil model. However, probably due to the support and dissemination by the GRL and PDI groups of their method and field monitoring techniques, these two have become presently the leading pile analysis methods and apparatuses in the industry.

There are many other methods of stress wave transmission that may be used. A wide selection of suitable wave equation may be found at the Internet website entitled "The Wave Equation Page for Piling" at http://www.geocities.com/CapeCanaveral/Hangar/2955.

Convention wave equation-based analysis procedure consists of, firstly, assuming the soil resistance parameters and, secondly, perform the dynamic trial analysis. Then, the measured results is compared with the computed pile top parameters. If the match is not satisfactory, new soil resistance parameters are computed and the dynamic trial analysis is performed again. If the soil model output matches satisfactorily, it may then proceed to simulated static test. A computer program such as GRLWEAP, CAPWAP, TNOWAVE, etc. may be used to perform repetitive and tedious analysis and correlation calculations of the porcedure.

The execution of such a program may be made automatic by a computational tool integrated with on-line data acquisition means to obtain and the parameters for running the program. An example of such integrated apparatus is PDI's Pile Driving Analyser™ or PDA™ which provides measurements taken on-line from a pile under driving hammer for the prediction method of static soil resistance.

Generally, the different parameters required for the execution of a wave equation analysis may be summarised in the following Table 2:

TABLE 2

SUMMARY OF PARAMETERS ESSENTIAL FOR WAVE EQUATION ANALYSIS

| Component | Parameter |
|---|---|
| Hammer | Model and efficiency. |
| Hammer cushion | Elastic modulus, area, thickness, and restitution coefficient. |
| Pile cap | Weight (including all cushion materials and inserts). |
| Pile cushion | Elastic modulus, area, thickness and coefficient of restitution. |
| Pile | Area, elastic modulus and mass density, all as a function of pile length. |
| Soil | Total static capacity, percent skin friction and its distribution, quake and damping values both at the pile toe and along the skin. |

The final result is a simulated static load test, representing the pile-soil behaviour at the time of testing. Hence, a re-strike test should be performed sometime after pile installation. If records are also evaluated at the end of installation, then the change of soil strength can be evaluated as a function of time.

OBJECTS OF THE INVENTION

The present invention endeavours to provide an alternative method for analysing and estimating a pile's load bearing capacity. Instead of using a wave equation, the present method employs the Impact Load Theory for both the simulated or virtual tests and actual field tests.

Basically, an "impact load" is a force delivered by a blow, as opposed to a force applied gradually and maintained over a long period. The Impact Load Theory is widely used in structural and mechanical engineering and may be found in any basic textbooks in such fields, for example in G. H. Ryder, *Strength of Materials,* 3rd ed, (1969), pages 9–12.

However, the Impact Load Theory is not known to have ever been applied in foundation or geotechnical engineering. Hence, the present invention proposes a new theoretical basis for estimating load bearing capacity of piles, i.e. by employing one or more equations derived from the Impact Load Theory.

SUMMARY OF THE INVENTION

The present invention provides for a method for estimating the load bearing capacity of a pile comprising obtaining the values of parameters including (i) the weight of an impact mass; (ii) the stroke height of the impact mass; (iii) the length of the pile; (iv) the cross sectional area of the pile; and (iv) the Young's modulus of the pile; and calculate said capacity using one or more equation derived from Impact Load Theory.

In one embodiment of the invention, the equation derived from the Impact Load Theory is $$P = W\left[1 + \sqrt{\frac{1 + 2hAE}{WL_e}}\right] \quad \text{Formula I}$$

wherein $P$ = the pile capacity;

$W$ = the weight of a hammer, being the impact mass $h$ = the height of hammer stroke;

$L_e$ = the length of pile;

$A$ = the cross sectional area of pile;

$E$ = the Young's modulus of pile.

In one specific embodiment of the invention, the equation derived from Formula I may be further derived and simplified to $$R = \sqrt{\frac{2AEWh}{L}} \quad \text{Formula II}$$

wherein $R$ = soil-resistance load, equivalent to $P$, load bearing of pile;

$W$ = the weight of hammer;

$h$ = the height of hammer stroke;

$L$ = the length of pile;

$A$ = the cross sectional area of pile;

$E$ = the Young's modulus of pile.

In another embodiment of the invention, the method may be used in designing and/or selecting a pile for its load bearing capacity, and in pile-driving control.

In yet another embodiment of the method, the estimated load bearing results calculated from a pile under design and/or selection according to the method may be compared with a corresponding result calculated according to conventional dynamic formulae, or, alternatively, a corresponding result calculated according to a method based on wave propagation theory.

Still another embodiment is to compare the capacity calculated according to the present method based on a pile being driven or tested with the corresponding capacity calculated according to a wave equation-based method using measurements of actual displacement of the pile being driven or under test. Alternatively, it may be compared with the corresponding results obtained from a static test.

In one preferred embodiment of the method, soil coefficient parameters may be included in the equation to refine the accuracy of estimation. Preferably still, the parameters and results are stored to build up a database for on-demand analysis of pile capacity.

The present invention also provides for an apparatus for estimating the load bearing capacity of a pile comprising a computational tool which accepts the values of parameters including the weight of a hammer, the stroke height of the hammer, the length of the pile, the cross sectional area of the pile, and the Young's modulus of the pile, and calculate said parameters according to an equation derived from the Impact Load theory.

In one preferred embodiment of the apparatus, the equation includes at least one of the above-stated Formulas I and II and the apparatus may be portable. In another preferred embodiment of the apparatus, the parameters are input online with data acquisition means from an actual pile under tests.

BRIEF DESCRIPTION OF DRAWINGS

To better understand the invention, the specific embodiments of the present method and apparatus will now be described in detail by way of example with reference to the following drawings in which:

FIG. 5 is a graph showing the correlation distribution of Case Method with PBC calculations and CAPWAP results with PBC calculations.

DETAILED DESCRIPTION OF SPECIFIC EMBODIMENTS

Figure 2A:
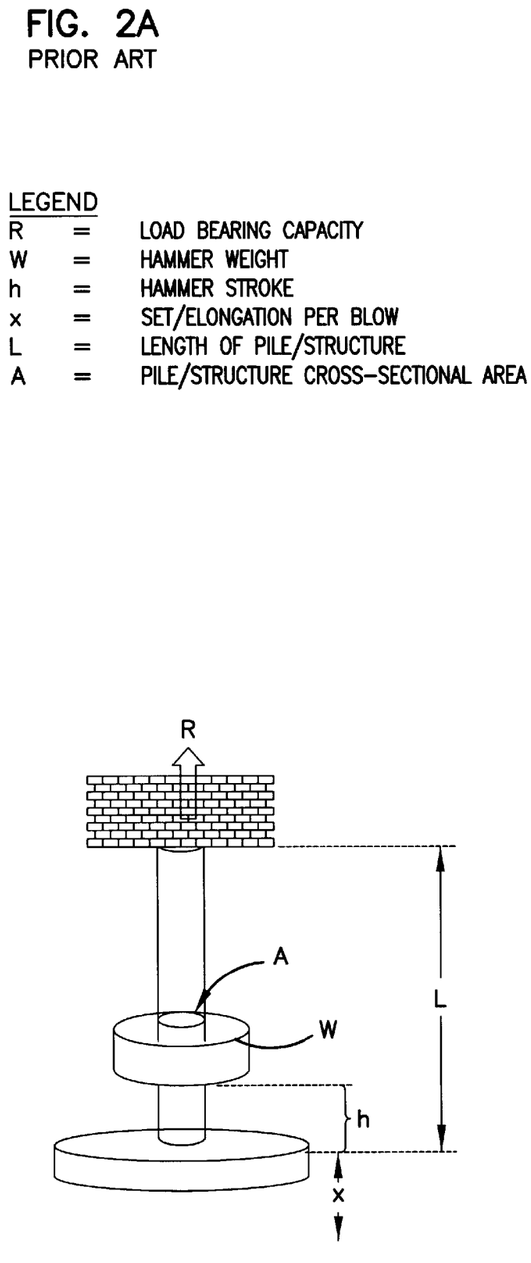
FIGS. 2A and 2B show in comparison the analogy of the pile driving model based on the Impact Load Theory with the conventional pile driving model being inverted.
Figure 2B:
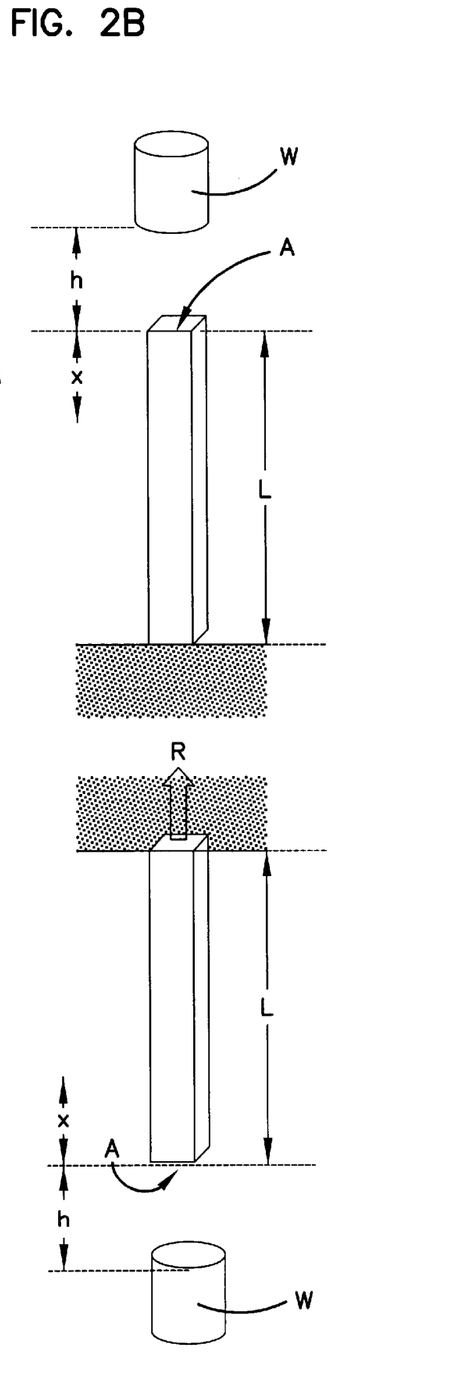

The Impact Load Theory as widely used in structural and mechanical engineering analysis may be simplified to as shown in FIG. 2A (from Ryder, ibid., FIG. 1.6, p. 9) and compared by way of analogy with an inverted model of the conventional pile driving arrangement as shown in FIG. 2B wherein the parameters required are as listed in the following Table 3.

TABLE 3

ANALOGY OF PILE DRIVING PARAMETERS

| parameter symbol | Impact Load model (FIG. 2A) | Conventional pile driving inverted model (FIG. 2B) |
|---|---|---|
| P, R | P, impact load on fixed end | R, end load bearing |
| A | cross sectional area of structural part under test | cross sectional area of pile under test |
| L | length of structural part under test | length of pile under test |
| W | weight of impact mass | weight of hammer |
| h | height of drop of impact mass | height of drop of hammer |
| s | extension of structural part as a result of impact mass drop | displacement of pile as a result of hammer drop |
| C | collar | pile cap |

In the Impact Load model of FIG. 2A, the weight of the impact mass W drops vertically through a height h onto a collar C attached to the lower end of a uniform bar, (i.e. the structural part under test) which upper end is fixed, whereupon extension x would result. The impact load P may be calculated according to the following formula (from Ryder, ibid, p. 9):

$$P = W\left[1 + \sqrt{\frac{1 + 2hAE}{WL_e}}\right] \quad \text{Formula I}$$

wherein $P$ = load applied at pile top;

$W$ = the weight of a hammer, being the impact mass $h$ = the height of hammer stroke;

$L_e$ = the length of pile;

$A$ = the cross sectional area of pile;

$E$ = the Young's modulus of pile.

Adapting this formula for normal pile driving behaviour where 1% to 2% of the hammer weight will be sufficient to drive the pile to achieve the desired load bearing capacity.

By substituting P≡100 W; the equation may be re-written as:

$$100W \Leftrightarrow W\left[1 + \sqrt{\frac{1 + 2hAE}{WL_e}}\right]$$

Reflecting on the components of this equation, it is realised that the factor $$\frac{2hAE}{WL_e}$$

is the dominant component; hence, the equation may be re-written as $$P = W\sqrt{\frac{2hAE}{WL_e}}$$

and then simplified to:

$$P = \sqrt{\frac{2hAEW}{L_e}} \quad \text{Formula II}$$

When we take the efficiency of the impact, e, into consideration, the equation becomes $$P = \sqrt{\frac{2AEWhe}{L_e}} \quad \text{Formula III}$$

The analogy and compatibility with the simplified version of Hiley's formula may be shown in the following (see Joseph E. Bowles, *Foundation Analysis and Design*, 4$^{th}$ ed. McGraw-Hill, pp 791–796 for a detailed version of Hiley's formula) based on FIG. 2B:

$$R = \frac{Whe}{s + \left(\frac{c}{2}\right)}$$

wherein $R$ = pile bearing capacity;

$W$ = hammer weight;

$h$ = hammer stroke;

$e$ = hammer efficiency;

$s$ = pile setting per blow;

$c$ = temporary compression;

$P$ = load applied at pile top;

$A$ = pile cross-sectional area; and $E$ = pile modulus.

Assuming there is no setting of pile, s=0; and known elastic shortening or temporary compression, c $$c = \frac{PL_e}{AE}$$

then Hiley's formula may be re-written as:

$$R = \frac{Whe}{PL_e/2AE}$$

and assuming there is force equilibrium, then action (load, P)=reaction (load bearing, R)

$$R^2 = \frac{Whe}{L_e/2AE} \therefore R = \sqrt{\frac{2AEWhe}{L_e}} \quad \text{Formula IV}$$

Hence, it appears that Formula IV is identical with Formula III.

As could be seen from a side-by-side comparison of FIG. 2A and FIG. 2B, Formula II is an analogy of the impact load applied to a pile to predict the pile bearing capacity. This formula is herein propounded as the theoretical basis for a now method for estimating the load bearing capacity of a pile. Depending on the purpose and availability of parameters, the method of the present invention may be used in (i) designing and/or (ii) selecting a pile for its load-bearing capacity, or (iii) controlling pile-driving.

(i) Pile selecting. By using any one of the above two Formulas, or other corresponding formulas derived from the Impact Load Theory, it would be relatively easy for a geotechnical engineer to calculate the estimated load-bearing capacity of a pile using the known parameters (as required in the above Formulas) of a particular pile. It may also be adapted or refined to include other parameters, including those listed in Table 3 above or other parameters such as hammer type or efficiency, pile cap characteristics, permanent setting of pile, etc.

(ii) Pile designing. Conversely, the engineer may be able to design a new pile based on the desired load-bearing capacity, specified material type or method of fabrication (e.g. whether reinforced concrete, spun concrete, steel, etc.), pile installation system and other parameters by using the method of the invention.

(iii) Pile driving control. As a related application, the method of the present invention may also be used in the control of pile driving, including selection of an appropriate pile driving system (e.g. whether to use a diesel, hydraulic, air/steam drive, free-fall or lifted drop, single acting or double acting hammer, etc.), height of stroke, suitable damping disc to be used, etc.

Pile Bearing Calculator & Comparative Studies

Figure 3:
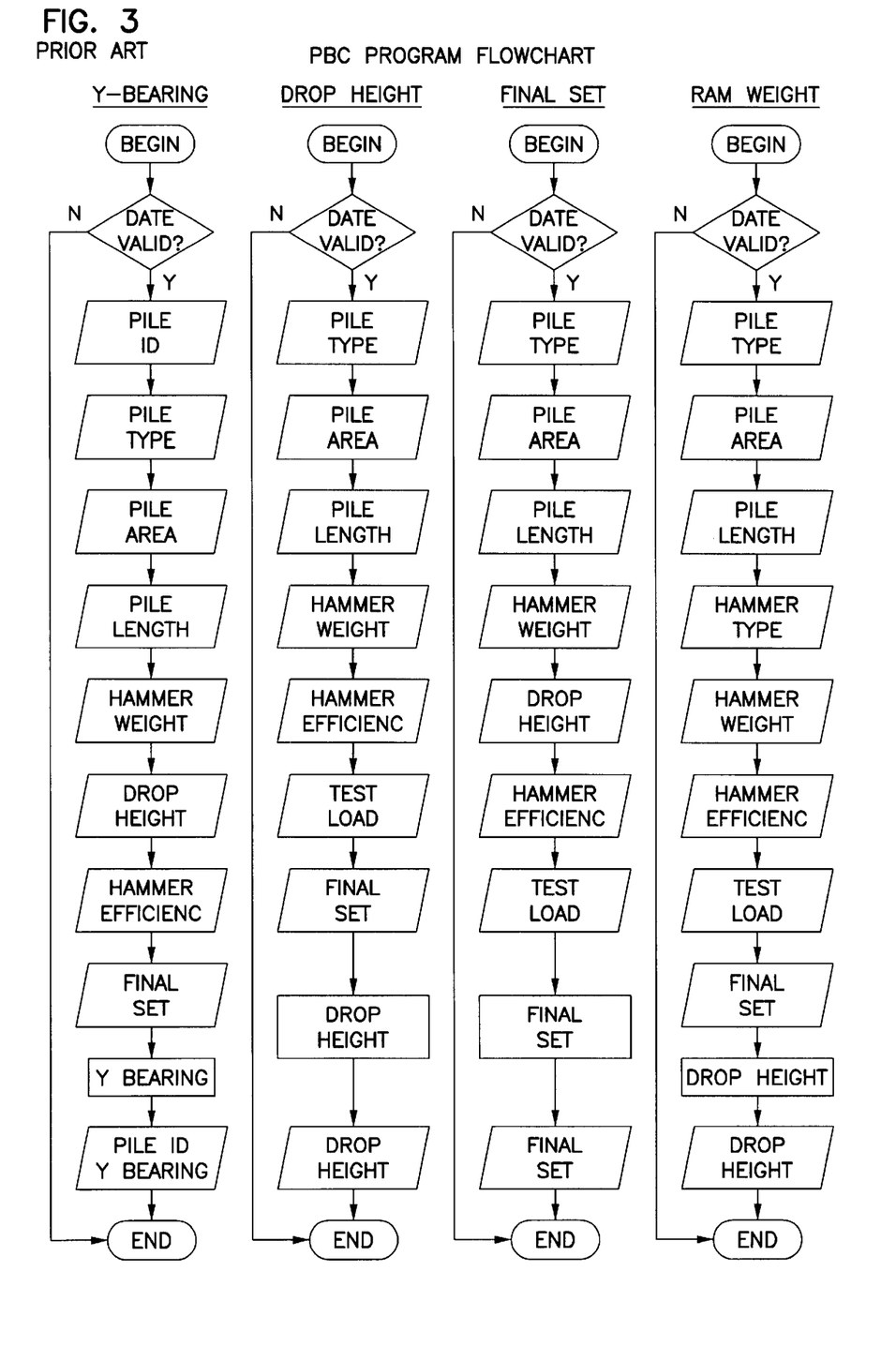
FIGS. 3 and 4 show an example of a flowchart for a program of the Pile Bearing Calculator (PBC).
Figure 4:
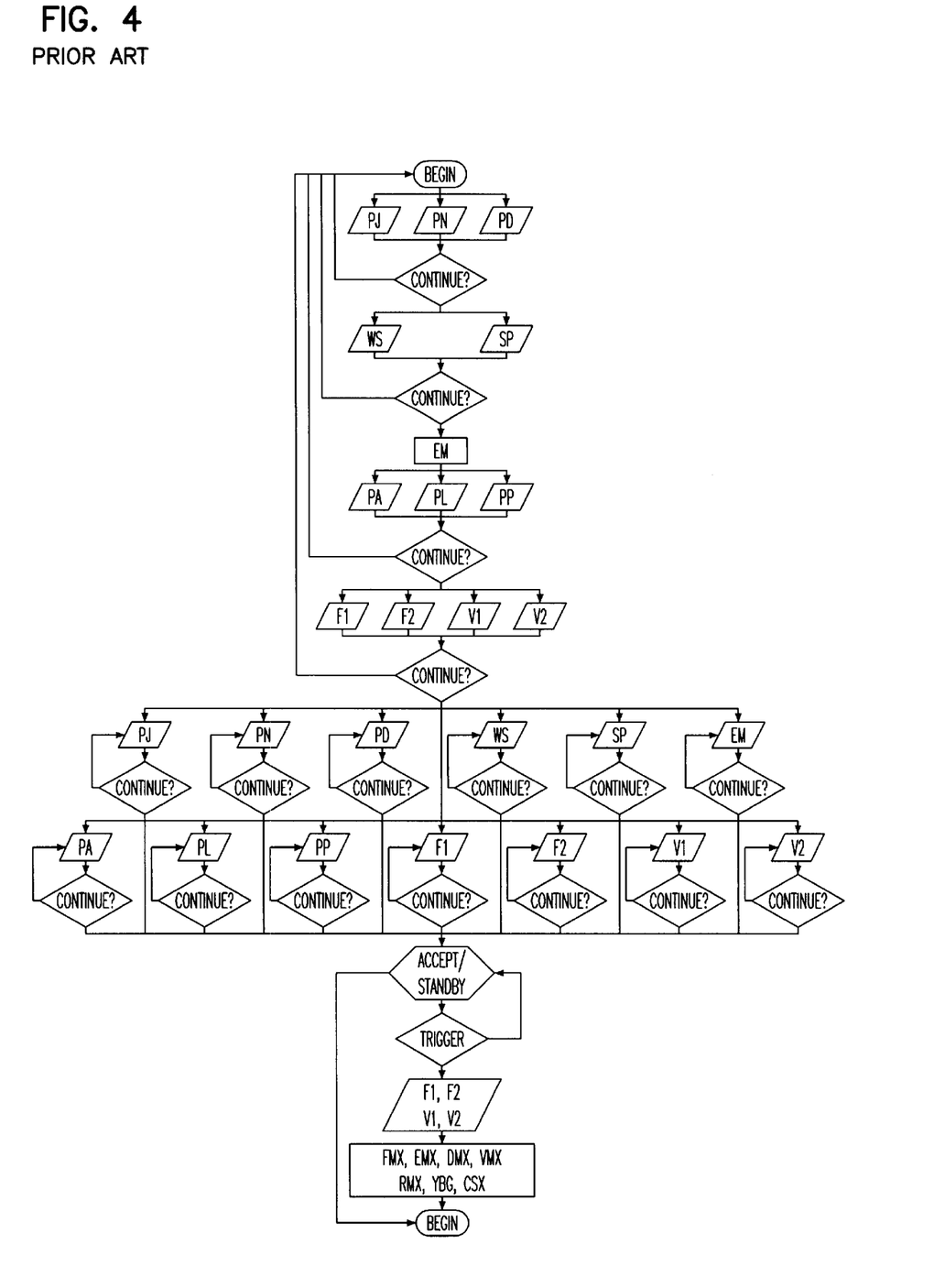

By incorporating the method of the present invention into a computational tool, such as a programmable calculator or virtual calculator (e.g. provided at a website over the Internet), the method of the invention many be applied in the field or site at ease. A program routine may be easily written based on a flowchart such as one shown in FIG. 3 and FIG. 4. With such a handy "Pile Bearing Calculator" (PBC), the pile bearing results calculated using the method of the present invention may be quickly and easily made. A comparison may be made of the PBC's calculated estimate results against the results of a number of cases obtained using the conventional Case Method, CAPWAP analysis and static tests.

As CAPWAP analysis is generally considered more accurate than the Case Method, the PBC's calculations has been compared against CAPWAP results of known or published cases. A sample size of 870 cases of piling data ranging from 150×150 mm² reinforced concrete piles to 1000 mm diameter steel pipe piles with test load from 40 to 700 tonnes have been analysed and recalculated according to the present method in this comparison study. The pile penetration lengths vary from 6 to 48 m with final set of 0 to 100 mm per 10 blows. These piles were tested by drop, hydraulic or diesel hammers.

The results are plotted as a correlation distribution graph in FIG. 5 in which the following annotation applies:

RMX: Maximum capacity computed by Case-Goble Method
RSX: Maximum capacity with Unloading Correction
CAPWAP: Computed capacity using Case Pile Wave Analysis Program
PBC: Pile bearing capacity predicted using Pile Bearing Calculator.

The values plotted are the results from Case and CAPWAP methods each divided by the results from the PBC calculations. Therefore, a value of 1.00 would indicate a perfect correlation and values beyond or below 1.00 would indicate deviation of the method of the present invention from the Case and CAPWAP methods.

As evident from the graph in FIG. 5, the correlation distribution of CAPWAP results falls within the acceptable standard deviations of 0.75 to 1.50. The distribution indicates that 23 samples of the CAPWAP results have standard deviations of more than 1.5 and 25 samples have less than 0.75. Most of the coordinates cluster around the 1.00 median and only 5.5% of the samples fall outside of the 0.75 to 1.50 range. Hence, it may be concluded that the method of the present invention as embodied in the PBC is as reliable as the CAPWAP analysis, Case Method and static tests.

The following are examples of specific cases of comparative correlation results between CAPWAP and PBC.

EXAMPLE 1

(Data from Richard Yu Ching Leong, "Evaluation of Static

Pile Capacity for Different Piles by Dynamic Testing",

Paper Published in *Bulletin IEM,* December 1989)

| CASE A | |
|---|---|
| Pile type: | Reinforced concrete |
| Pile size: | 355 mm × 355 mm |
| Pile depth: | 23.2 m |
| Hammer type: | 5-tonne hydraulic hammer |
| Drop height: | 0.9 m |
| Final set: | 10 mm/blow |
| Type of test: | End of drive |
| RESULTS: | |
| PDA | 93 tonnes |
| PBC | 167 tonnes |
| Standard Deviation | 0.56 |

Notes: At the end of the driving test, PDA recorded maximum force of about 150 tonnes. A maximum force of about 250 tonne was recorded during restrike test 5 hours later. By assuming all the parameter such as pile length, pile size, hammer type & drop height are the same with similar final set (10 and 8 mm per blow), it is therefore expected that the measured force should be similar. As this is not the case, it is possible that certain parameter input was wrong in the first (end of drive) test. Assuming the pile capacity is proportionate to the imparted force, the corrected results should be:

Imparted force=150 tonne, corrected to imparted force= 250 tonne;

PDA result=93 tonne, corrected to PDA result=155 tonne;

Hence, the corrected standard deviation=0.93

| CASE B | |
|---|---|
| Pile type: | Reinforced concrete |
| Pile size: | 355 mm × 355 mm |
| Pile depth: | 23.2 m |
| Hammer type: | 5-tonne hydraulic hammer |
| Drop height | 0.9 m |
| Final set: | 8 mm/blow |
| Type of test: | 5 hours after installation |
| RESULTS: | |
| CAPWAP | 160 tonnes |
| PBC | 167 tonnes |
| Standard Deviation | 0.96 |

| CASE C | |
|---|---|
| Pile type: | Cast in situ pile |
| Pile Size: | 1050 diameter |
| Pile depth: | 45.5 m |
| Hammer type: | 6.7-tonne drop hammer |
| Drop height: | 5 m |
| Final set: | 0 mm/blow (assumed) |
| Type of test: | End of drive |
| RESULTS: | |
| CAPWAP | 1225 tonnes |
| PBC | 1177 tonnes |
| Standard Deviation | 1.04 |

EXAMPLE 2

(Data from S. L. Lee, et. al. "Dynamic Testing of Bored Piles for

Suntec City Development", Published at Conference on Deep

Foundation Practice in Singapore, October 1990)

| Summary of parameters: | |
|---|---|
| Total piles: | 2600 bored piles |
| Size: | 0.8 to 1.6 m diameter |
| Depth: | 20 to 60 m below ground surface |
| Total PDA tests: | 80 tests |
| Ram weight | 25-tonne drop hammer |
| Drop height | 1.8 to 3.5 m |
| Analysed by | CAPWAP, NUSWAP |
| Cushion thickness | 75 to 100 mm plywood |
| Working load for 1.0 m diameter | 550 tonnes |
| Working load for 1.2 m diameter | 800 tonnes |
| Prediction of hammer drop height | GRLWEAP, NUSWAP & Fugro McClelland's version. |

| Area (cm$^2$) | Total length (m) | Drop height (m) | Mobilised pile capacity | | |
|---|---|---|---|---|---|
| | | | NUSWAP (MN) | CAPWAP (MN) | Case (0.5) (MN) |
| 7854 | 28 | 2.0 | 17.5 | 19.3 | 16.6 |
| 7854 | 28 | 2.0 | 16.9 | 18.4 | 17.5 |
| 11310 | 42 | 2.5 | 21.1 | 20.9 | 19.5 |
| 11310 | 39 | 2.5 | 19.6 | 21.0 | 19.5 |
| 11310 | 37 | 2.5 | 20.0 | 21.2 | 20.2 |
| 11310 | 36 | 2.5 | 21.4 | 22.5 | 21.9 |

| Mobilised pile capacity | | | | Standard deviation | | |
|---|---|---|---|---|---|---|
| PBC (MN) | NUSWAP (MN) | CAPWAP (MN) | Case (0.5) (MN) | NUSWAP | CAPWAP | Case (0.5) |
| 14.9 | 17.5 | 19.3 | 16.6 | 1.17 | 1.29 | 1.11 |
| 14.9 | 16.9 | 18.4 | 17.5 | 1.13 | 1.23 | 1.17 |
| 19.1 | 21.1 | 20.9 | 19.5 | 1.10 | 1.09 | 1.02 |
| 19.8 | 19.6 | 21.0 | 19.5 | 0.99 | 1.06 | 0.98 |
| 20.4 | 20.0 | 21.2 | 20.2 | 0.98 | 1.04 | 0.99 |
| 20.7 | 21.4 | 22.5 | 21.9 | 1.04 | 1.09 | 1.06 |

(assumed permanent set at PDA tests = 0)

Site Testing of Piles

The method of the present invention may also be used in estimating the capacity of an driven or installed pile by calculating the parameters obtained from measuring live or actual field tests on said driven pile. The load-bearing capacity estimated according to the invention may then be compared with the corresponding capacity calculated according to a wave equation-based method using measurements of actual displacement of the pile being driven or under test.

The method of the invention may be applied by adopting an appropriate formula derived from the Impact Load Theory (instead of the conventional dynamic or wave equation formulae) for calculations in a procedure modified from the conventional dynamic pile testing procedure as in the following example.

EXAMPLE 3

Impact Load Pile Testing Procedure (i) A preliminary Impact Load equation analysis is performed (e.g. using the "Pile Bearing Calculator" or PBC, q.v. above) based on subsurface conditions (obtained from soil boring tests or soil investigations reports), pile type, pile capacity and type of pile driving or hammer system proposed to be used.

(ii) Piles are then driven at locations specified by the foundation engineer using the driving criteria established by the Impact Load equation above, subject to any changes due to actual hammer stroke results and expected soil strength changes during pile driving. Dynamic testing is made during the final driving as may be prescribed under conventional practices (e.g. for concrete piles, test is conducted throughout the pile installation process; for fine grain soils, alternate piles are tested; install a specified number of piles to varying penetrations and/or driving resistance, etc.) and, if necessary, repeat the tests.

(iii) After a prescribed minimum waiting period (which depends on the soil description) the designated test piles are evaluated by re-striking them with simultaneous PBC (q.v.) testing. The re-strike testing is considered important for determining load capacity so that set-up, relaxation or settlement effect or the pile is to be considered. This is because the method of the present invention and the PBC calculates the pile capacity at the time of testing.

(iv) Accordingly, testing of additional piles may ordered by the foundation engineer during additional construction control visits either on the initially installed structured and/or restrike, as the soil conditions may dictate and depending on the size of the project. Further dynamic tests may be recommended if, for example, the hammer system is replaced or modified, if different behaviour from the expected or standard practice is observed, to determine if any characteristic changes have occurred to the hammer, pile or soil.

(v) Perform analysis of the measured data with PBC, or any equivalent computational tool using an Impact Load formula, on a certain percentage of the piles tested to verify field results. As each site has unique and often unforeseen characteristics, judgements by the supervising geotechnical engineer should be made, even during the testing program, as to omissions or additions to a standard program which will result in the most benefit.

(vi) The results obtained on certain parameters such as (i) the driving stresses (compression and, for concrete piles, tension); (ii) pile integrity; (iii) hammer system efficiency; (iv) pile bearing capacity, etc. are then reviewed and a report or summary of the results submitted upon completion of the tests.

Pile Bearing Analyser (PBA)

In another preferred embodiment of the apparatus, the data for input as parameters in the PBC may be acquired on-line during actual tests with suitable data acquisition means and analysed by a suitable data processing machine with output. The three basic components of such a pile bearing analyser (PBA) apparatus are:

(i) transducers (for sensing strain and acceleration and converting it to signal);

(ii) data acquisition system for receiving the signals from the transducers, converting and conditioning the signals for processing by a data processing machine; and (iii) a portable data processing machine such as a computer.

Specification for Data Processing Machine

E.g. a notebook computer. For ease of transportation to the field and moving from pile to pile at site, a sturdy portable or notebook computer having the following specifications would be most suitable.

bright non-reflective screen (e.g. TFT) so as to display sufficiently under the bright outdoor sun;

two serial ports (e.g. one RS-232; the other RS-232/422 selectable);

support for a floppy disk drive;

operating temperature range: −10 to +50° C.;

humidity range: 0 to 95% RH, non-condensing;

shock: withstand up to 20 g.

Specification for Data Acquisition System

A data acquisition module considered suitable is one which components are encased compactly and small enough to be coupled to the notebook computer. Such a module preferably has:

PCMCIA—A/D converter card with signal conditioning (dual 14-bit, 300 kHz) for coupling to the notebook computer's PCMCIA slot;

8 single-ended analog input channels (2×4);

sampling rate at minimum 5000 Hz;

automatic gain control and automatic zero levelling;

battery pack or 12V DC adapter for car's cigarette lighter battery jack.

Specification for Transducers Connectors, etc.

There are many types of transducers, including combined strain-acceleration transducers. Depending on the manufacturers, mounting rigs may be provided for ease of mounting the transducers onto the pile under test. Due to the roughness of the construction sites, it is essential that the transducers, connectors, cables and junction boxes are of high quality, durable and specially designed for such harsh conditions.

Where direct contact with a pile to be tested is not possible or where a remote method of measuring is necessary, the strain-acceleration transducers may be substituted with impulse radar transducers where the signal generated is a very high frequency electromagnetic pulse.

It is apparent to a skilled person that soil coefficient parameters may be included in any of the equations of the present invention to refine the accuracy of estimation since the principle of load-bearing of a pile does not depend on the pile's parameters alone but rather on the "soil-pile" system.

It is also obvious to a skilled person that the parameters and results from the method of the present invention may be stored to build up a database until its sampling size becomes large enough for on-demand correlation analysis of pile capacity, independent from an analysis using the method of the invention.

It will be apparent to a person skilled in the art that the specific embodiments described hereinabove may be varied or substituted with equivalent parts or components which are not specifically described herein. For example, instead of the PBC being a portable programmable calculator, it may be a calculator non-programmable to the user with its ROM pre-programmed with the method of the invention. These equivalents, variations or substitutes may be used to effectively work the concept and working principles of this invention and they are not to be considered as departures from the present invention and which shall be considered as falling within the letter and spirit of the following claims.

What is claimed is:

1. A method for estimating the load bearing capacity of a pile comprising obtaining the values of parameters which include:

the weight of an impact mass;

the stroke height of the impact mass;

the length of the pile;

the cross sectional area of the pile; and the Young's modulus of the pile;

and calculate said capacity using one or more equations derived from Impact Load Theory.

2. A method according to claim 1 wherein the equation derived from the Impact Load Theory is:

$$P = W\left[1 + \sqrt{\frac{1 + 2hAE}{WL_e}}\right] \quad \text{Formula I}$$

wherein $P$ = the pile capacity;

$W$ = the weight of a hammer, being the impact mass $h$ = the height of hammer stroke;

$L_e$ = the length of pile;

$A$ = the cross sectional area of pile;

$E$ = the Young's modulus of pile.

3. A method according to claim 2 wherein the equation of Formula I is further derived and simplified to:

$$P = \sqrt{\frac{2hAEW}{L_e}} \quad \text{Formula II}$$

wherein $P$ = soil-resistance load or end-load bearing;

$W$ = the weight of hammer;

$h$ = the height of hammer stroke;

$L_e$ = the length of pile;

$A$ = the cross sectional area of pile;

$E$ = the Young's modulus of pile.

4. A method according claim 1 for use in designing and/or selecting a pile for its load bearing capacity.

5. A method according to claim 1 for use in pile-driving control.

6. A method according to claim 1 for use in estimating the capacity of an driven pile based on actual field tests conducted on said driven pile.

7. A method according to claim 4 wherein the estimated load bearing results calculated from a pile under design and/or selection is compared with a corresponding result calculated according to conventional dynamic formulae.

8. A method according to claim 4 wherein the estimated load bearing results calculated from a pile under design and/or selection is compared with a corresponding result calculated according to a method based on wave propagation theory.

9. A method according to claim 5 wherein the calculated pile capacity is compared with the corresponding capacity calculated according to a wave equation-based method using measurements of actual displacement of the pile being driven or under test.

10. A method according to claim 6 wherein the calculated pile capacity is compared against corresponding results which has been obtained from a static test.

11. A method according to claim 1 wherein soil coefficient parameters are included in the equation to refine the accuracy of estimation.

12. A method according to claim 1 wherein the parameters and results are stored to build up a database for on-demand correlation analysis of pile capacity.

13. An apparatus for estimating the load bearing capacity of a pile comprising a computational tool which accepts the values of parameters including:

the weight of a hammer the stroke height of the hammer;

the length of the pile;

the cross sectional area of the pile; and the Young's modulus of the pile;

and calculate said parameters according to an equation derived from the Impact Load theory.

14. An apparatus according to claim 13 wherein the equation includes at least one of Formulas I and II and wherein the computational tool is portable.

15. An apparatus according to claim 13 wherein the parameters are input online with data acquisition means from an actual pile under tests.

* * * * *